US010408671B2

United States Patent
Mirov et al.

(10) Patent No.: US 10,408,671 B2
(45) Date of Patent: *Sep. 10, 2019

(54) INTEGRATED WEARABLE NOISE DOSIMETER

(71) Applicant: Verily Life Sciences LLC, Mountain View, CA (US)

(72) Inventors: Russell Norman Mirov, Los Altos, CA (US); John Lapetina, Los Altos Hills, CA (US); Florence Thng, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/125,932

(22) Filed: Sep. 10, 2018

(65) Prior Publication Data

US 2019/0003878 A1    Jan. 3, 2019

Related U.S. Application Data

(63) Continuation of application No. 14/698,155, filed on Apr. 28, 2015, now Pat. No. 10,072,967.

(51) Int. Cl.
*G01H 3/10* (2006.01)
*A61B 5/0205* (2006.01)
(Continued)

(52) U.S. Cl.
CPC ............. *G01H 3/10* (2013.01); *A61B 5/0205* (2013.01); *A61B 5/165* (2013.01); *A61B 5/4818* (2013.01);
(Continued)

(58) Field of Classification Search
CPC ... G01H 3/14; G01H 3/10; A61B 5/11; A61B 5/14542; A61B 5/0205; A61B 5/742;
(Continued)

(56) References Cited

U.S. PATENT DOCUMENTS 3,692,959 A * 9/1972 Lamp .................... H04R 25/30
                                                              381/60
4,020,286 A * 4/1977 Ceci ......................... G01H 3/12
                                                              341/139
(Continued)

FOREIGN PATENT DOCUMENTS

JP      H08-94428       4/1996
WO      2014/198570     12/2014

OTHER PUBLICATIONS

International Searching Authority, International Search Report and Written Opinion dated Jun. 21, 2016, issued in connection with International Patent Application No. PCT/US20161026132, filed Apr. 6, 2016, 14 pages.

(Continued)

*Primary Examiner* — Toan M Le
(74) *Attorney, Agent, or Firm* — McDonnell Boehnen Hulbert & Berghoff LLP

(57) ABSTRACT

Systems and methods are described that may provide audio information about an environment around a wearable device. Such audio information may be correlated with other biometric data to provide physiological information, e.g. regarding a wearer of the wearable device. For example, an illustrative method includes receiving an audio signal via a microphone of a wearable device and rectifying the audio signal with a peak detector. The method further includes amplifying the rectified signal with a logarithmic amplifier and causing an analog to digital converter (ADC) to sample the logarithmic signal. The method also includes causing the ADC to convert the sampled logarithmic signal to a digital output and storing the digital output in a memory of the wearable device. In some embodiments, the method includes transmitting the digital output to a computing device, which may correlate the digital output with other biometric data.

20 Claims, 6 Drawing Sheets

(51) Int. Cl.
*A61B 5/00* (2006.01)
*G01H 3/14* (2006.01)
*H04R 29/00* (2006.01)
*A61B 5/16* (2006.01)
*A61B 5/021* (2006.01)
*A61B 5/024* (2006.01)
*A61B 5/053* (2006.01)
*A61B 5/08* (2006.01)
*A61B 5/11* (2006.01)
*A61B 5/145* (2006.01)
*A61B 7/00* (2006.01)

(52) U.S. Cl.
CPC ............ *A61B 5/681* (2013.01); *A61B 5/6891* (2013.01); *A61B 5/742* (2013.01); *A61B 5/7405* (2013.01); *G01H 3/14* (2013.01); *H04R 29/008* (2013.01); *A61B 5/021* (2013.01); *A61B 5/024* (2013.01); *A61B 5/0533* (2013.01); *A61B 5/0816* (2013.01); *A61B 5/11* (2013.01); *A61B 5/14542* (2013.01); *A61B 5/4815* (2013.01); *A61B 5/6803* (2013.01); *A61B 5/7246* (2013.01); *A61B 7/003* (2013.01); *A61B 2560/0242* (2013.01)

(58) Field of Classification Search
CPC ..... A61B 5/7405; A61B 5/7246; A61B 5/165; A61B 5/4818; A61B 5/681; A61B 5/0816; A61B 5/0533; A61B 5/024; A61B 5/021; H04R 29/008
See application file for complete search history.

(56) References Cited

U.S. PATENT DOCUMENTS

| | | | |
|---|---|---|---|
| 4,220,160 A * | 9/1980 | Kimball | A61B 7/04 381/67 |
| 4,726,057 A | 2/1988 | Doerry et al. | |
| 5,131,046 A * | 7/1992 | Killion | H03G 9/18 330/254 |
| 7,495,998 B1 | 2/2009 | Deligeorges et al. | |
| 8,398,538 B2 | 3/2013 | Dothie et al. | |
| 8,771,204 B2 | 7/2014 | Telfort et al. | |
| 10,072,967 B2 * | 9/2018 | Mirov | A61B 5/0205 |
| 2006/0241510 A1 | 10/2006 | Halperin et al. | |
| 2008/0294019 A1 | 11/2008 | Tran | |
| 2013/0102908 A1 | 4/2013 | Ser et al. | |
| 2014/0247154 A1 | 9/2014 | Proud | |

OTHER PUBLICATIONS

Young, Tom, "Everything You Wanted to Know About Sound Level Meters (SLMs)," Pro Sound Web, Jan. 27, 2012, 8 pages.

* cited by examiner

INTEGRATED WEARABLE NOISE DOSIMETER

CROSS-REFERENCE TO RELATED APPLICATION

This application is a continuation of, and claims the benefit of priority from, U.S. patent application Ser. No. 14/698,155, filed Apr. 28, 2015, which is hereby incorporated herein by reference in its entirety.

BACKGROUND

An environmental monitoring device may provide information about a sound pressure level of an environment around the monitoring device.

SUMMARY

In a first aspect, a system is provided. The system includes a microphone configured to provide an audio signal and a rectifier communicatively coupled to the microphone. The system also includes a logarithmic amplifier communicatively coupled to the rectifier. A combination of the logarithmic amplifier and the rectifier is configured to provide a rectified logarithmic signal based on a mathematical log function and the audio signal. The system additionally includes an analog to digital converter (ADC) communicatively coupled to the logarithmic amplifier. The ADC is configured to sample the rectified logarithmic signal and provide a digital output based on the sampled rectified logarithmic signal. The system further includes a controller that includes a memory and a processor. The controller is configured to carry out instructions. The instructions include, at predetermined time intervals, causing the ADC to sample the rectified logarithmic signal and storing the digital output in the memory. The instructions also include transmitting the digital output to a computing device. The computing device is configured to correlate the digital output with other biometric data.

In a second aspect, a system is provided. The system includes a microphone configured to provide an audio signal, a logarithmic amplifier communicatively coupled to the microphone, a rectifier communicatively coupled to the logarithmic amplifier, an analog to digital converter (ADC) communicatively coupled to the rectifier, and a controller. The logarithmic amplifier is configured to provide a logarithmic signal based on a mathematical log function and the audio signal. The rectifier is configured to provide a rectified signal based on the logarithmic signal. The ADC is configured to sample the rectified signal and provide a digital output based on the sampled rectified signal. The controller includes a memory and a processor. The controller is configured to carry out instructions. The instructions include, at predetermined time intervals, causing the ADC to sample the rectified signal and storing the digital output in the memory. The instructions also include transmitting the digital output to a computing device. The computing device is configured to correlate the digital output with other biometric data.

In a third aspect, a system is provided. The system includes a microphone configured to provide an audio signal, a rectifier communicatively coupled to the microphone, an analog to digital converter (ADC) communicatively coupled to the rectifier, and a controller. The rectifier is configured to provide a rectified signal based on the audio signal. The ADC is configured to sample the rectified signal and provide a digital output based on the sampled rectified signal. The controller includes a memory and a processor. The controller is configured to carry out instructions. The instructions include, at predetermined time intervals, causing the ADC to sample the rectified signal and storing the digital output in the memory. The instructions also include providing a logarithmic output based on a mathematical log function and the digital output. The instructions further include transmitting the digital output to a computing device, wherein the computing device is configured to correlate the digital output with other biometric data.

In a fourth aspect, a method is provided. The method includes receiving an audio signal via a microphone of a wearable device and rectifying the audio signal with a rectifier to provide a rectified signal. The rectifier includes a peak detector. The method further includes amplifying the rectified signal with a logarithmic amplifier to provide a logarithmic signal based on a mathematical log function and the rectified signal. The method also includes causing an analog to digital converter (ADC) to sample the logarithmic signal. The method yet further includes causing the ADC to convert the sampled logarithmic signal to a digital output. The method additionally includes storing the digital output in a memory of the wearable device. The method also includes transmitting the digital output to a computing device. The computing device is configured to correlate the digital output with other biometric data.

Other aspects, embodiments, and implementations will become apparent to those of ordinary skill in the art by reading the following detailed description, with reference where appropriate to the accompanying drawings.

DETAILED DESCRIPTION

Figure 1A:
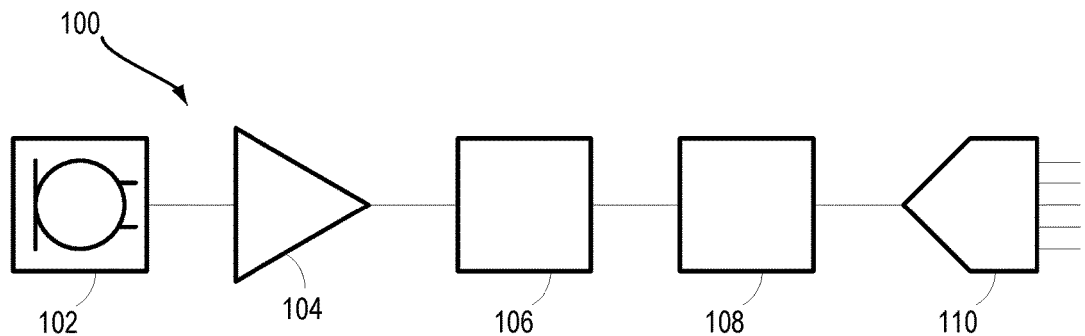
FIG. 1A illustrates a system, according to an example embodiment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

The present disclosure discloses embodiments in which a device is configured to record data related to an acoustic environment around the device. For example, a sound pressure level (SPL) of the environment around the device may be recorded and tracked over a long period of time (e.g. weeks, months, and/or years). The SPL data may relate to a particular environment (e.g. a room or an area in the case of a static device) and/or a local environment around the device (e.g. near a wearer of a wearable device). SPL data may be useful to track medical conditions such as breathing, sleep apnea, or environmental conditions, such as ambient noise levels in a work environment, at concerts, etc. In an example embodiment, the SPL data may be detected and processed using a wearable biotelemetry device. Alternative uses may include home security or environmental monitoring systems.

In an example embodiment, a wearable device may be configured to measure and record SPL data without the possibility of capturing intelligible acoustic content, e.g. without recording actual conversations or other recognizable sounds. For example, the wearable device may include a small form factor microphone. The microphone may be a device that transduces sounds, e.g. pressure waves in air, into an electrical signal. The microphone may operate based on electromagnetic induction, piezoelectricity, or a change in capacitance, among other modes of operation. The signal produced by the microphone may be amplified by a pre-amplifier circuit (which may be a component of the microphone). In some embodiments, however, a pre-amplifier is not present.

The signal from the pre-amplifier circuit may be passed through a rectifying circuit that may modify the signal. Rectifying circuits may include an envelope detector, a peak detector, and/or a trough detector, among other types of rectifying circuits. For example, a peak detector may include a rectifying circuit that includes at least one capacitive element. Furthermore, the peak detector may be configured to provide an output signal based on the peak amplitude of the unprocessed signal.

The rectifying circuit may produce a relatively slowly changing voltage that may represent the instantaneous amplitude of the audio waveform. The response time of the circuit is slow enough such that individual syllables of speech are detectable, but not identifiable. In an example embodiment, the response time of the circuit may be configured to distinguish a respiration rate (or snoring) from conversation or other identifiable sounds.

Within the scope of the present disclosure, the rectifying circuit may include analog signal processing hardware. By performing the signal rectification using analog hardware (versus software or digital signal processing), security and privacy concerns may be reduced or eliminated. For example, it may be more difficult to obtain identifiable or recognizable audio signals when the recorded signals are passed substantially directly to signal processing hardware without intervening digital signal handling.

Before and/or after the signal is rectified, the signal may be passed through a logarithmic amplifier (Log Amp). The Log Amp may be configured to convert a voltage signal to decibels. The Log Amp may additionally or alternatively include filters with controlled response to provide different "weightings" to the detected audio based on, for instance, the frequency components of the signal. For example, the output of the Log Amp may convert and/or translate the voltage signal to a signal that may relate to decibel A-weighting (dBA).

In an example embodiment, decibel A-weighting may be applied to the logarithmic signal, which may convert the logarithmic signal to a recognized measure of SPL. Specifically, dBA has been adopted as an environmental noise measurement standard and may offer a comparison between the detected audio signals and well-known real-world noise sources (rock concert, airplane takeoff, etc.). Other frequency-related weightings are possible, including, but not limited to, B-, C-, D-, and Z-weightings.

The output of the Log Amp may be passed to an analog to digital converter (ADC). The output of the ADC may be saved locally and/or transmitted to cloud storage and/or cloud computing devices. Uploading to cloud storage and/or cloud computing devices may occur in "real time." Alternatively or additionally, uploading could occur periodically at predetermined time intervals, or at other times.

The microphone, rectifier, the Log Amp, and/or other components of the system may be configured to handle audio signals at +20 dBA or quieter. For example, the system may be configured to capture breathing, gasping, or talking noises from a wearer of the wearable biotelemetry device. Accordingly, the system may include components configured to reduce or minimize signal noise, e.g. low noise preamplifiers, noise filters, etc. Additionally or alternatively, some or all of the components of the system may be configured to handle relatively loud audio signals (e.g. +120 dBA or louder). Accordingly, the system may be configured to handle a large range of SPL values, such as multiple signal gain and/or attenuation stages.

Example embodiments may include several different variations regarding the order of how signals are processed in the system. For instance, the signal may pass through the Log Amp before passing through the rectifier circuit, or vice versa. Other combinations of rectification, amplification, and/or filtering may be implemented under the scope of the present disclosure.

Other processing and/or sampling may be performed on the signal using hardware or software. For instance, an analog to digital converter (ADC) may be configured to sample the signal as sampled data. The signal may be sampled at frequencies such as 50 Hz or 60 Hz, but other sampling frequencies are possible. The sampled data may be stored locally, for example in system memory. Alternatively or additionally, the sampled data may be uploaded to a network (e.g. a cloud server), which may store or aggregate data about noise levels.

In an example embodiment, a system may include a microphone, a pre-amplifier, a peak detector, a log amplifier, and an analog to digital converter (ADC). In another example embodiment, a system may additionally or alternatively include a trough detector. The system may include hardware and/or software configured to perform the functions of a log amplifier. Additionally or alternatively, further functions (e.g. filtering) may be performed using further signal processing hardware and/or software.

In an example embodiment, the sampled data may be correlated with other biometric data or parameters. For example, a sleep apnea condition may be diagnosed and/or treated by correlating the sampled SPL and/or dBA data with respiration and/or movement data of the wearer of a biotelemetry device. Alternatively, for example to measure sleep quality, the sampled SPL and/or dBA data may be correlated with other data such as blood pressure, heart rate, blood oxygen saturation, respiration, and/or movement. In another example related to measuring stress level, the sampled SPL and/or dBA data may be correlated with heart rate, blood pressure, and/or galvanic skin response. In yet another example, mental health and/or general health issues related to speech may be tracked using the sampled SPL and/or dBA data in conjunction with other data such as movement. Many other data correlations may be made with the sampled SPL data. The data correlations may be performed by a computing device, which may be a wearable biotelemetry device or another computing device, such as a cloud computing network.

II. System Examples

FIG. 1A illustrates a system 100, according to an example embodiment. System 100 includes a microphone 102 configured to provide an audio signal. That is, the microphone 102 may be configured to convert an acoustic sound or a sound pressure level into the audio signal, which may be an electrical signal. The microphone 102 may be one of, or any combination of, a fiber optic microphone, a dynamic microphone, a condenser microphone, an electret condenser microphone, a ribbon microphone, a MEMS microphone, and/or a piezoelectric microphone. Other types of microphones are contemplated herein. The microphone 102 may be integrated into another electronic device, e.g. a smartphone or a wearable computing device. Alternatively or additionally, the microphone 102 may be an externally coupled to another device, e.g. via a cable.

The system 100 may include a pre-amplifier 104. The pre-amplifier 104 may amplify an electrical signal from the microphone 102. In an example embodiment, the pre-amplifier 104 may apply gain to the electrical signal from the microphone 102. The pre-amplifier 104 may include one or more gain stages. In an example embodiment, the pre-amplifier 104 may be incorporated into, and/or housed with, the microphone 102. In other embodiments, the pre-amplifier 104 is not included in the system 100.

The system 100 also includes a rectifier 106 communicatively coupled to the microphone 102 or the pre-amplifier 104. The rectifier 106 may convert a varying or alternating current into a direct current. The rectifier 106 may be a stand-alone part or the rectifier may include electronic components arranged in an electrical circuit. For example, the rectifier 106 may include a silicon diode, a thyristor, a crystal rectifier, or another type of rectifier. In an example embodiment, the rectifier 106 includes a single-phase, half-wave rectifier circuit. However, other rectifier circuits are contemplated herein, e.g. a single-phase, full-wave rectifier circuit. In an example embodiment, the rectifier 106 may include a filter circuit. Thus, in such situations, the rectifier 106 may provide filtering and/or other types of signal processing to the audio signal.

The rectifier 106 is configured to provide a rectified signal based on the audio signal. In an example embodiment, the rectifier 106 includes a peak-hold circuit, which may also be termed a peak detector or an envelope detector. The peak detector may take as its input the audio signal provided by the microphone 102 or pre-amplifier 104 and may output the peak output voltage of the audio signal. In an example embodiment, the peak detector may include adjustable characteristics, such as attack time and/or decay time. The peak detector may be configured to "hold" a peak voltage for a much longer time than the peak voltage may exist in the input audio signal. The peak detector circuit may include at least one operational amplifier, a diode, and a capacitor. Additionally or alternatively, the peak detector circuit may include a point contact device. Other types of circuits configured to rectify a varying electrical signal and/or track a peak amplitude of the varying electrical signal are contemplated herein.

The system 100 also includes a logarithmic amplifier 108 communicatively coupled to the rectifier 106. The logarithmic amplifier 108 is configured to provide a logarithmic signal based on a mathematical log function and the rectified signal from the rectifier 106. Namely, the logarithmic amplifier 108 may provide an output voltage that is a multiple of the natural logarithm of the input voltage. The logarithmic amplifier 108 may include one or more amplification or gain stages, e.g. four 30-dB amplification stages. The logarithmic amplifier 108 may be similar or identical to a Maxim AN 36211 or a Texas Instruments TL441. In an example embodiment, the logarithmic amplifier 108 includes a baseband logarithmic amplifier or a demodulating logarithmic amplifier.

The system 100 may include the rectifier 106 and logarithmic amplifier 108 in various arrangements. For example, the signal flow may go through the rectifier 106 and then the logarithmic amplifier 108, or vice versa. In an example embodiment, a combination of the rectifier 106 and the logarithmic amplifier 108 may provide a signal that is both rectified and modified (e.g. multiplied) based on a mathematical log function. In such a scenario, the provided signal may be a rectified logarithmic signal.

The system 100 also includes an analog to digital converter (ADC) 110 communicatively coupled to the logarithmic amplifier 108. The ADC 110 is configured to convert the continuous time, continuous amplitude signal from the logarithmic amplifier 108 to a discrete time, discrete amplitude digital signal. Namely, the ADC 110 is configured to sample the rectified logarithmic signal and provide a discrete digital output proportional to the sampled rectified logarithmic signal. The discrete digital output may include a conversion error at least based on the bit resolution of the ADC 110. The ADC 110 may have a 16-bit resolution, however other resolutions are possible. The sampling rate of the ADC 110 may be 10-100 samples per second, however other sampling rates are possible.

The system 100 may be configured to detect and record sounds as quiet as +20 dBA (e.g., breathing) and as loud as +120 dBA (e.g., a concert). Thus, system 100 may be configured and/or designed with low-noise components and multiple gain stages to provide a low noise floor and wide dynamic range.

Figure 1B:
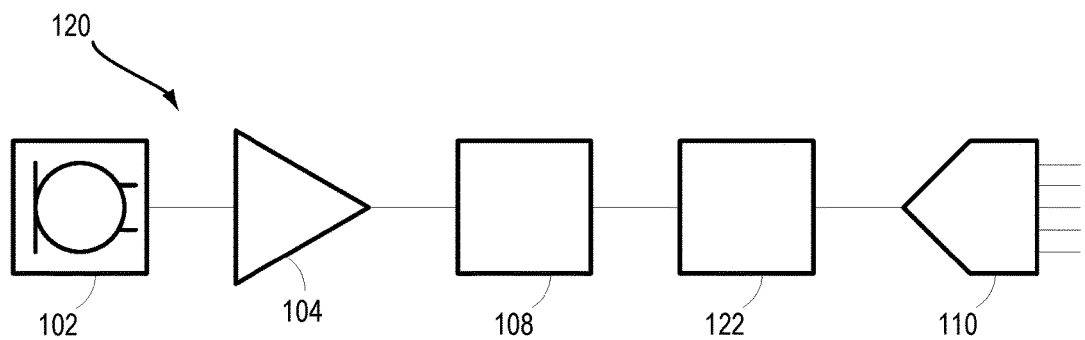
FIG. 1B illustrates a system, according to an example embodiment.
Figure 1C:
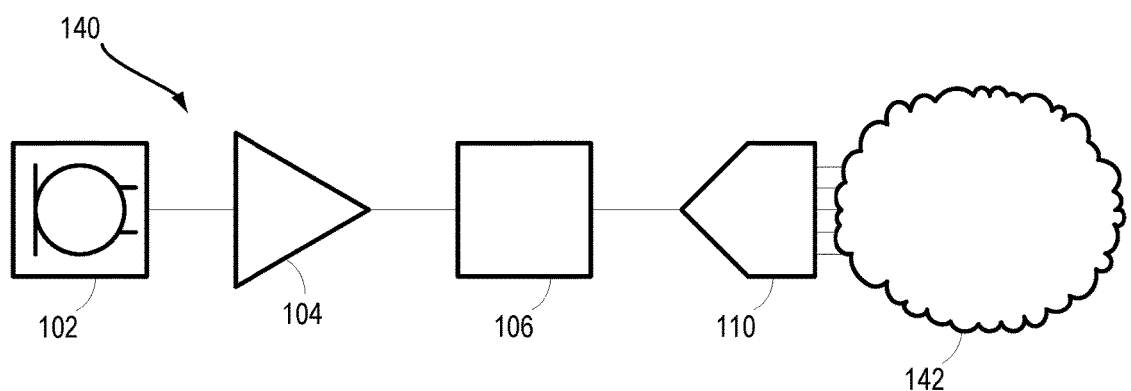
FIG. 1C illustrates a system, according to an example embodiment.

Other arrangements of some or all of the elements of system 100 are possible. For example, FIGS. 1B and 1C illustrate two such other arrangements. FIG. 1B illustrates a system 120, according to an example embodiment. System 120 may include a microphone 102 and a pre-amplifier 104 arranged similarly to system 100 as illustrated and described in reference to FIG. 1A. System 120 may include a logarithmic amplifier 108 communicatively coupled to the microphone 102 and/or the pre-amplifier 104. The logarithmic amplifier 108 may be configured to provide a logarithmic signal based on a mathematical log function and the audio signal, as described above.

System 120 may further include a trough detector 122 communicatively coupled to the logarithmic amplifier 108. The trough detector 122 may be a rectifier configured to track the audio signal and hold a voltage level based on a minimum level, magnitude, and/or amplitude of the audio signal. The system 120 may also include the ADC 110 communicatively coupled to the trough detector 122.

In some embodiments, the system 120 may include a trough detector 122 or a peak detector based on a polarity of the logarithmic amplifier 108. Additionally or alternatively, the rectifier 106 and/or the trough detector 122 may include a peak excursion detector. Other signal processing devices configured to modify a sound and provide output signal, such that the output signal is unidentifiable or untraceable to one or more people who produced the sound, are considered herein.

As a further alternative, FIG. 1C illustrates a system 140, according to an example embodiment. System 140 may include a microphone 102, a pre-amplifier 104, and a rectifier 106 with a similar arrangement as that in system 100, illustrated and described in reference to FIG. 1A. System 140 may also include the ADC 110 communicatively coupled to the rectifier 106.

System 140 may include a digitized output of the ADC 110 being handled, modified, and/or processed by a computer according to software instructions 142. The software instructions 142 may be stored as non-transitory computer readable media. Further, software instructions 142 may be stored in a memory and the software instructions 142 may be executed by a processor. The computer may modify the digitized output of the ADC 110 by performing one or more functions according to the software instructions 142. The one or more functions may include a logarithmic multiplication. In other words, the software instructions 142 and processor may be configured to provide a logarithmic amplification of the digitized signal from the ADC 110. The software instructions 142 may be configured to carry out further functions on the digitized signal.

It is understood that other combinations of analog and/or digital signal processing stages, components, or other elements are possible within the scope of this disclosure.

Figure 2:
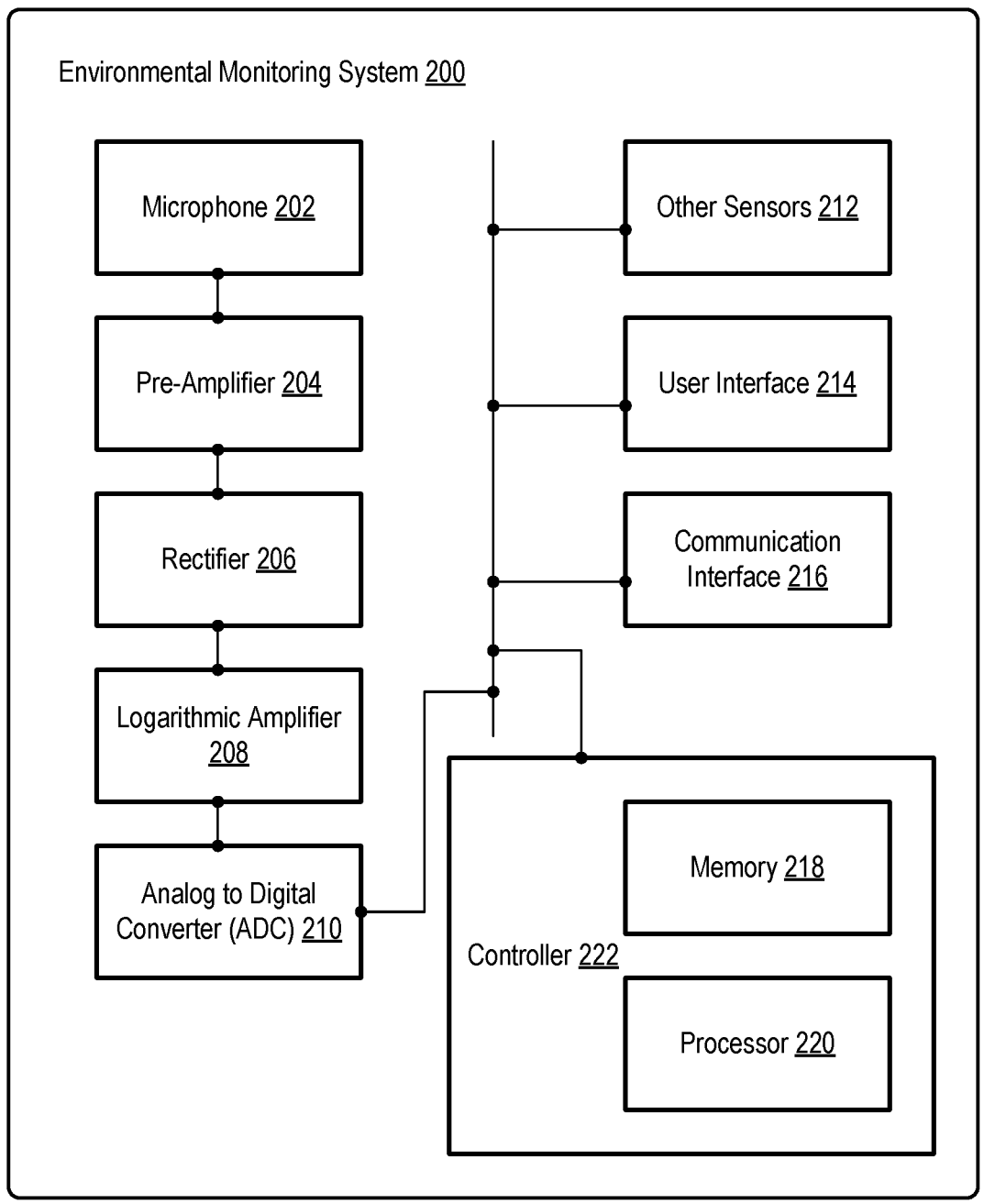
FIG. 2 illustrates a schematic block diagram of an environmental monitoring system, according to an example embodiment.

FIG. 2 illustrates a schematic block diagram of an environmental monitoring system 200, according to an example embodiment. The environmental monitoring system 200 may include some or all of the same elements as systems 100, 120, and/or 140, as illustrated and described in reference to FIGS. 1A, 1B, and 1C, respectively. In an example embodiment, environmental monitoring system 200 includes a microphone 202, a pre-amplifier 204, a rectifier 206, a logarithmic amplifier 208, and an ADC 210, which may be communicatively coupled in a series arrangement. Such an arrangement of elements may operable to provide a digitized signal that relates to an acoustic environment around the environmental monitoring system 200. As described above, other arrangements of the microphone 202, pre-amplifier 204, rectifier 206, logarithmic amplifier 208, and/or the ADC 210 are possible.

The environmental monitoring system 200 may also include other sensors 212. The other sensors 212 may include one or more sensors configured to measure, monitor, qualify and/or quantify various biometric data. Many types of biometric data are contemplated within the scope of this disclosure. For example, the other sensors 212 may be configured to measure blood pressure, heart rate, galvanic skin response, respiration, analyte concentration, movement, blood oxygen saturation, or other biometric data.

The environmental monitoring system 200 may further include a user interface 214. The user interface 214 may include a display, a touchscreen, one or more indicator lights, or another type of interface configured to provide information to a user and/or to obtain input from a user. In an example embodiment, the user interface 214 may include a touchscreen display that provides information indicative of the sound pressure level of the environment around the environmental monitoring system 200.

The environmental monitoring system 200 may include a communication interface 216. The communication interface 216 may be operable to provide a wired and/or wireless connection to another computing device and/or a computing network, e.g. the Internet and/or a cloud computing system. In an example embodiment, the communication interface 216 may be a wireless network interface controller, which may interact with a wireless network via a communication protocol such as IEEE 802.11, ZIGBEE, and/or BLUETOOTH.

The environmental monitoring system 200 may further include a controller 222. The controller 222 may include a memory 218 and a processor 220. The controller 222 is configured to carry out instructions. The instructions may include, at predetermined time intervals, causing the ADC 210 to sample the logarithmic signal. For example, the controller 222 may cause the ADC 210 to sample the logarithmic signal at a sampling rate, e.g. 50 samples/second. The instructions may also include storing the digital output from the ADC 210 in the memory 218.

The instructions may further include transmitting the digital output to a computing device. In an example embodiment, the transmitting may include transmitting the digital output to another computing device via communication interface 216. In another embodiment, the transmitting may include transmitting the digital output to the controller 222. In both scenarios, the computing device may be configured to correlate the digital output with other biometric data. The other biometric data may include any data obtained by the other sensors 212. Additionally or alternatively, the other biometric data may include data calculated and/or inferred by a computing device based on one or more further types of biometric data.

Figure 3:
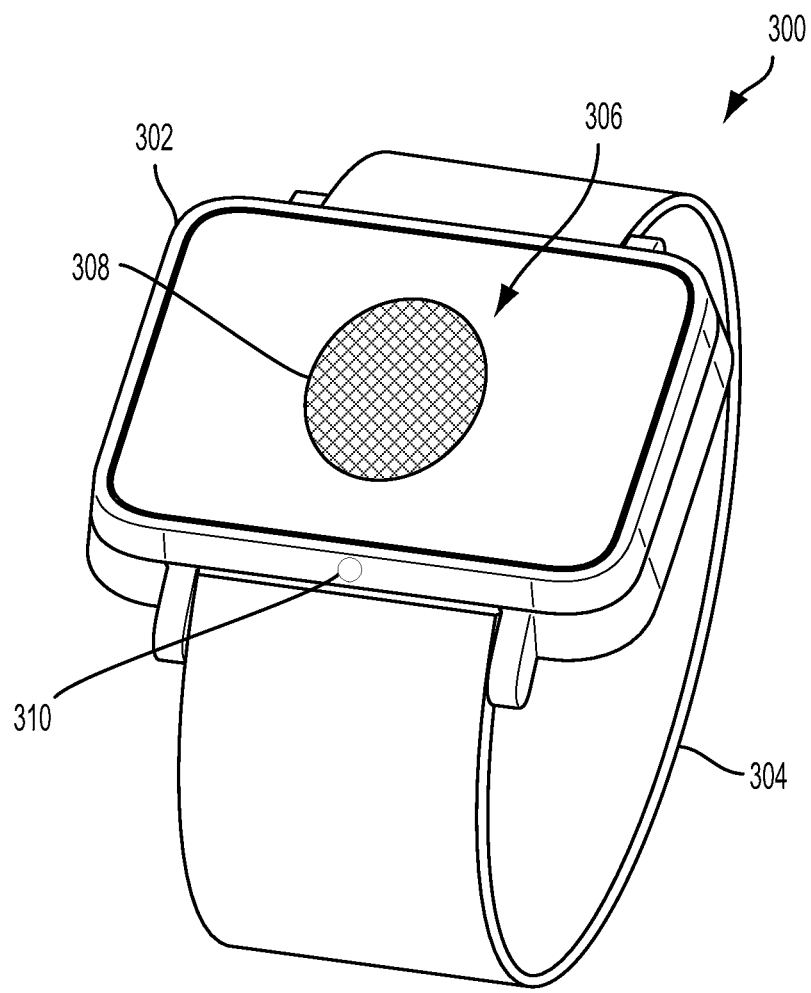
FIG. 3 illustrates a wearable device, according to an example embodiment.

FIG. 3 illustrates a wearable device 300, according to an example embodiment. The wearable device 300 may be worn around an arm, similar to a watch. Alternatively or additionally, the wearable device 300 may be worn around a neck (e.g. a necklace), and/or at other locations. In an example embodiment, the wearable device 300 may include a face 302 and a band 304. The band 304 may be operable to fasten the wearable device 300 to an arm and/or a wrist of a user. In the alternative, it is understood that band 304 may include a necklace, chain, adhesive, or another mechanical device configured to couple the wearable device 300 to a user.

The face 302 may include a display 306. The display 306 may be a touchscreen, however, other types of displays and/or indicators are contemplated. In an example embodiment, the display 306 may provide an indication 308 to a user. The indication 308 may include information indicative of a sound pressure level (SPL) of the environment of the wearable device 300.

In an example embodiment, the wearable device 300 may include a microphone 310. The microphone 310 may be the microphone 102 or 202, as illustrated and described in reference to FIGS. 1A-1C and 2. The microphone 310 may be operable to record the SPL of an environment around the wearable device 300. SPL data may capture sounds made by the user, particularly during sleep, such as gasping for breath, snoring, sneezing, wheezing, and/or other breathing sounds. Additionally, SPL data may include sounds nearby the user, such as an ambient noise level. Sound level data may be saved by the wearable device 300 and/or uploaded to another computing device.

Any or all of the elements of environmental monitoring system 200 may be incorporated, fully or in part, into the wearable device 300. For example, the wearable device 300 may include other sensors configured to detect other types of biometric data, such as heart rate and blood pressure. By combining SPL data with the other biometric data, various inferences may be made regarding the health of a user of the wearable device 300.

For example, in an effort to measure sleep quality, the sampled SPL data may be correlated with other data such as blood pressure, heart rate, blood oxygen saturation, respiration, and/or movement. That is, if SPL data indicates gasping for breath during sleep and the user's blood oxygen saturation is below a predetermined level, an inference may be made that a user's sleep quality may be poor.

Furthermore, the SPL data in combination with other biometric data may be useful to help provide health professionals with evidence to support a particular diagnosis. As an example, if, during sleep, a) SPL data indicates snoring and gasping for breath, b) the user's blood pressure is elevated above a predetermined level, and c) a movement rate was high, an inference may be made that the user may be suffering from a sleep apnea condition. Other health related inferences and/or diagnoses may be made based on the SPL data as well as the SPL data in combination with other biometric data.

In a scenario where a user may be suffering from a medical condition, the system and methods herein may include further functions and/or instructions configured to provide biometric feedback to a user in an effort to provide treatment and/or alleviate symptoms related to the medical condition. In an example embodiment, biometric data obtained by the systems and methods described herein may be used to determine a sleep apnea condition. In such a scenario, the system may provide a local notification (e.g. a subconscious or conscious alert) to "nudge" the user back into a normal sleep pattern. For example, the system may be configured to provide audio feedback, e.g. the controller may cause an audio feedback device and a speaker to state: "roll onto your side," "insert your oral appliance," or "please wear your CPAP device." Other types of user feedback are possible, such as a vibration alert, a chime, or another type of alert.

In another example related to measuring stress level, the sampled SPL and/or dBA data may be correlated with heart rate, blood pressure, stress-related analytes, and/or galvanic skin response. In such a scenario, a correlation that suggests an elevated stress level may trigger an indication 308 to a user of the wearable device 300. For example, an indication 308 such as, "Take a deep breath", "Go for a run", or "Practice mindfulness for 5 minutes" may be presented to the user of the wearable device 300 via the display 306 in an effort to reduce the user's stress level.

In yet another example, mental health and/or general health issues related to speech may be tracked using the sampled SPL and/or dBA data in conjunction with other data such as movement. For example, a user of the wearable device 300 may speak a phrase once a day, once a week, or over a different period. The sampled SPL data associated with the verbalized phrase may change over time, which may indicate a change in verbal, mental, and/or physical ability. As such, the SPL data may be used to track, diagnose, and/or evaluate the changing condition of the user over a period of time.

It is understood that SPL data and/or other biometric data may be recorded and correlated over a variety of time periods. For instance, SPL data may be monitored and/or stored over days, weeks, months, or years.

While FIG. 3 illustrates a wearable device 300, various elements of environmental monitoring system 200 may be incorporated into other types of devices. For example, some or all of the elements of environmental monitoring system 200 may be incorporated into a static device as part of a home appliance or another type of substantially fixed or static device.

Figure 4A:
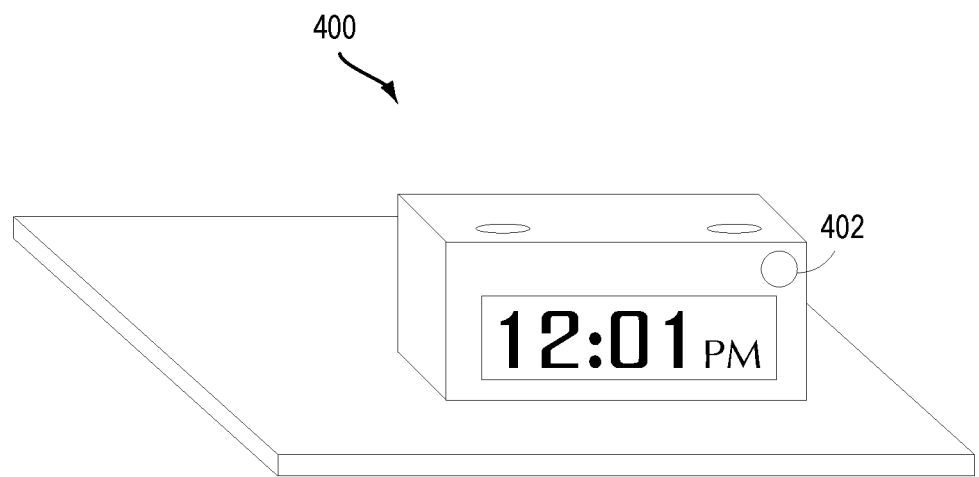
FIG. 4A illustrates a device, according to an example embodiment.

FIG. 4A illustrates a device 400, according to an example embodiment. Device 400 may be configured to have some or all of the functionality of a clock radio or similar device. In an example embodiment, device 400 may be placed near a bedside or another sleep environment. Device 400 may include microphone 402, which may be similar or identical to microphone 202 as illustrated and described in reference to FIG. 2.

Figure 4B:
FIG. 4B illustrates a device, according to an example embodiment.

FIG. 4B illustrates a device 410, according to an example embodiment. Device 410 may be configured to have some or all the functionality of a thermostat and/or another type of environmental monitoring device. Device 410 may include a microphone 412, which may be similar or identical to microphone 202 as illustrated and described in reference to FIG. 2.

It is understood that environmental monitoring system 200 may take the form of, or be incorporated into, a variety of different objects, systems, and/or devices. For example, environmental monitoring system 200 may be incorporated into a wall-mounted clock, a "wall-wart" plug, a smoke detector, a carbon monoxide detector, a glass-break sensor, a smartphone, a tablet, a desktop computer, or any number of other objects. These other possible embodiments are contemplated herein.

Figure 5:
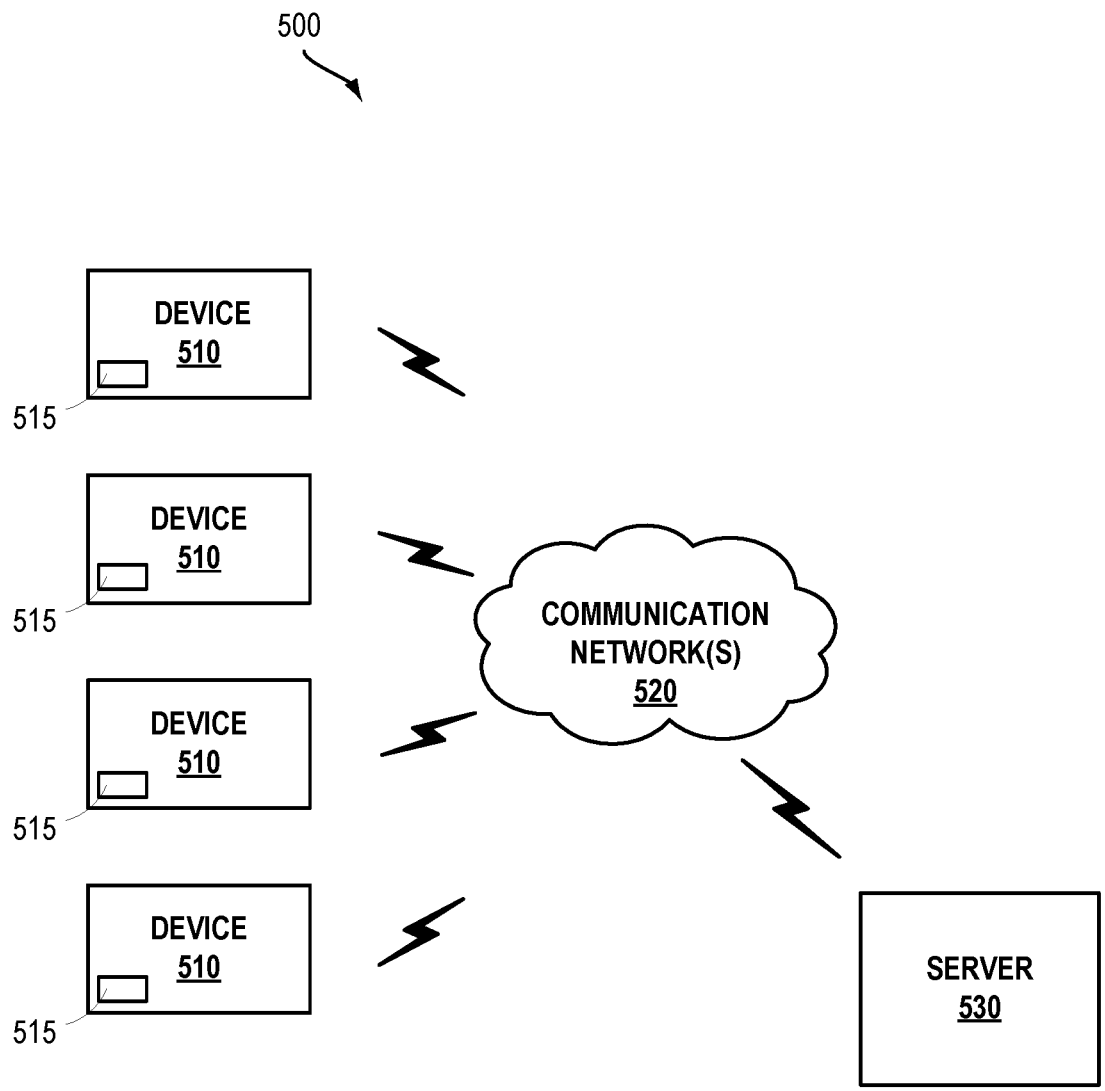
FIG. 5 illustrates a system, according to an example embodiment.

FIG. 5 illustrates a system 500, according to an example embodiment. System 500 may include a plurality of devices 510, which may be similar or identical to environmental monitoring system 200. Each of the plurality of devices 510 may include one or more sensors 515. The one or more sensors 515 may be operable to provide SPL data and/or biometric data as described elsewhere herein. Each of the plurality of devices 510 may be configured to provide the SPL and/or the other biometric data to a server 530 via one or more communication networks 520. The server 530 may perform some or all of the correlations between the SPL data and the biometric data.

In an example embodiment, the plurality of devices 510 may be located in physical proximity to one another, e.g. within the same building, near a concert venue, within a same neighborhood or another shared environment. In such a scenario, SPL data from the plurality of devices 510 may be aggregated to obtain an average sound pressure level of the shared environment. Such aggregate SPL data may be useful to monitor noise levels at a job site and/or in a residential setting. Other uses for aggregated SPL data are possible.

III. Method Examples

Figure 6:
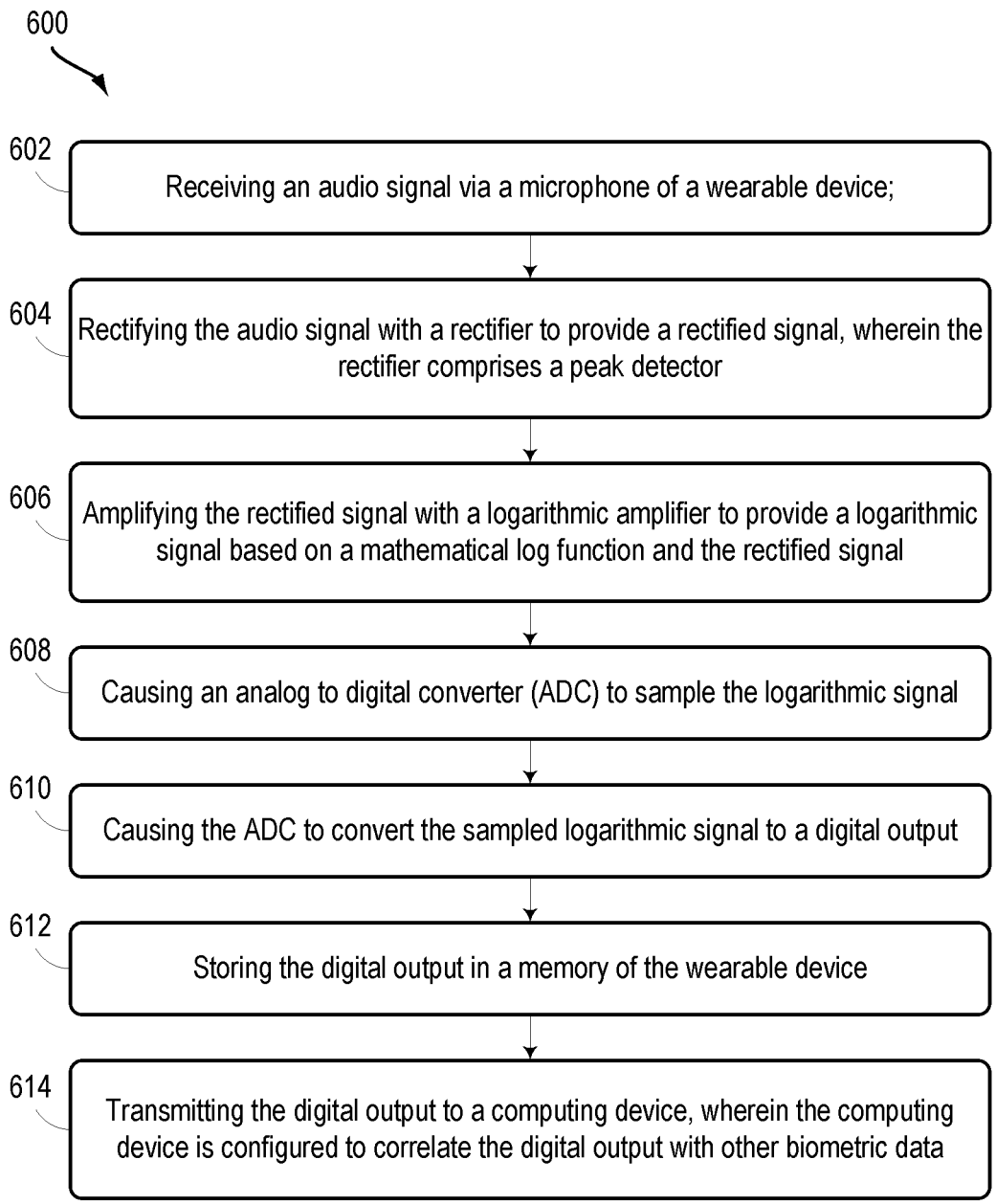
FIG. 6 illustrates a method, according to an example embodiment.

FIG. 6 illustrates a method 600, according to an example embodiment. The method 600 includes blocks that may be carried out in any order. Furthermore, various blocks may be added to or subtracted from method 600 within the intended scope of this disclosure. The method 600 may correspond to steps that may be carried out using any or all of the devices and systems illustrated and described in reference to FIGS. 1A-1C, 2, 3A-3B, 4A-4B, and 5.

Block 602 includes receiving an audio signal via a microphone of a wearable device. The audio signal may include sounds in an environment around and/or near the wearable device. The audio signal may have an associated sound pressure level, as described herein. The wearable device may include the wearable device 300, as illustrated and described in relation to FIG. 3. Alternatively, the wearable device may include a different wearable computing device or mobile device, such as a smartphone or a tablet. The microphone may include a built-in microphone of the wearable device. Alternatively or additionally, the microphone may include an external microphone.

Block 604 includes rectifying the audio signal with a rectifier to provide a rectified signal. In an example embodiment, the rectifier includes a peak detector. The peak detector could be similar or identical to the peak-hold circuit described in reference to system 100.

Block 606 includes amplifying the rectified signal with a logarithmic amplifier to provide a logarithmic signal based on a mathematical log function and the rectified signal. As described elsewhere herein, the logarithmic amplifier may be configured to provide a logarithmic signal based on a mathematical log function and the signal from the peak-hold circuit.

Block 608 includes causing an analog to digital converter (ADC) to sample the logarithmic signal. In an example embodiment, a controller, such as controller 222 described in reference to FIG. 2, may control a sampling trigger and/or the sampling rate of the ADC. In such a scenario, the controller may be configured to cause the ADC to sample the logarithmic signal at a sampling rate, such as 10-100 samples/second. Other sampling rates are possible.

Block 610 includes causing the ADC to convert the sampled logarithmic signal to a digital output. Converting the sampled logarithmic signal may include digitizing the logarithmic signal by performing a bit conversion. In an example embodiment, the ADC may include a bit resolution of 16-bits. In such a scenario, the analog logarithmic signal may be converted into a 16-bit digitized output based on an amplitude or another characteristic of the logarithmic signal.

Block 612 includes storing the digital output in a memory of the wearable device. In other words, the digitized output from the ADC may be stored in a memory, such as the memory 218 of environmental monitoring system 200. Alternatively, the digital output need not be stored locally at the wearable device, but may rather be directly uploaded or otherwise transmitted to another computing device.

Block 614 includes transmitting the digital output to a computing device. Transmitting the digital output may include uploading the digital output to the computing device via a communications interface, such as communication interface 216 of environmental monitoring system 200. The computing device may include a server, a computing network, and/or a cloud computing network. The computing device may be configured to correlate the digital output with other biometric data, so as to form inferences or provide evidence for the diagnosis of various health-related conditions.

As described elsewhere herein, the wearable device may include at least one other sensor, which may be configured to obtain other biometric data. The other biometric data may include, but should not be limited to, respiration data, movement data, blood pressure data, heart rate data, blood oxygen saturation data, and galvanic skin response data.

The particular arrangements shown in the Figures should not be viewed as limiting. It should be understood that other embodiments may include more or less of each element shown in a given Figure. Further, some of the illustrated elements may be combined or omitted. Yet further, an illustrative embodiment may include elements that are not illustrated in the Figures.

While various examples and embodiments have been disclosed, other examples and embodiments will be apparent to those skilled in the art. The various disclosed examples and embodiments are for purposes of illustration and are not intended to be limiting, with the true scope being indicated by the following claims.

What is claimed is:

1. A method comprising:
receiving an audio signal;
rectifying and amplifying the audio signal to provide a rectified and logarithmically amplified signal based on a mathematical log function;
sampling the rectified and logarithmically amplified signal to provide a sampled rectified and logarithmically amplified signal;
converting the sampled rectified and logarithmically amplified signal to a digital output;
transmitting the digital output to a computing device, wherein the computing device is configured to correlate the digital output with other biometric data; and
triggering an indication relating to a user's health via a user interface, wherein the indication is based on a comparison between the digital output and the other biometric data.

2. The method of claim 1, wherein the rectifying and the amplifying the audio signal are performed in an analog domain.

3. The method of claim 1, wherein the method is performed by a wearable device.

4. The method of claim 3, wherein the wearable device comprises a microphone, wherein receiving the audio signal is performed by way of the microphone.

5. The method of claim 1, further comprising obtaining the other biometric data.

6. The method of claim 5, wherein obtaining the other biometric data is performed by at least one other sensor.

7. The method of claim 1, wherein the other biometric data comprises at least one of: respiration data, movement data, blood pressure data, heart rate data, blood oxygen saturation data, or galvanic skin response data.

8. The method of claim 1, wherein the amplifying of the audio signal is performed by a logarithmic amplifier, wherein the logarithmic amplifier comprises a baseband logarithmic amplifier.

9. The method of claim 1, wherein the amplifying of the audio signal is performed by a logarithmic amplifier, wherein the logarithmic amplifier comprises a demodulating logarithmic amplifier.

10. The method of claim 1, wherein the rectifying of the audio signal is performed by a peak detector circuit, wherein the peak detector circuit comprises a rectifier circuit and a filter circuit.

11. A system comprising:
analog hardware configured to:
provide an audio signal; and
rectify and logarithmically amplify the audio signal to provide a rectified and logarithmically amplified signal based on a mathematical log function;
an analog to digital converter (ADC); and
a controller comprising a memory and a processor, wherein the controller executes instructions stored in the memory so as to carry out operations, the operations comprising:

at predetermined time intervals, causing the ADC to sample the rectified and logarithmically amplified signal and provide a digital output;

transmitting the digital output to a computing device, wherein the computing device is configured to correlate the digital output with other biometric data; and triggering an indication relating to a user's health via a user interface, wherein the indication is based on a comparison between the digital output and the other biometric data.

12. The system of claim 11, wherein the rectified and logarithmically amplified signal is an analog signal.

13. The system of claim 11, wherein the analog hardware comprises a microphone configured to provide the audio signal.

14. The system of claim 11, wherein the analog hardware comprises a rectifier and a logarithmic amplifier, wherein the rectifier and the logarithmic amplifier are configured to provide the rectified and logarithmically amplified signal.

15. The system of claim 14, wherein the rectifier comprises a peak detector circuit, wherein the peak detector circuit comprises a rectifier circuit and a filter circuit.

16. The system of claim 14, wherein the rectifier comprises a trough detector circuit.

17. The system of claim 14, wherein the logarithmic amplifier comprises a baseband logarithmic amplifier or a demodulating logarithmic amplifier.

18. The system of claim 11, further comprising a wearable device, wherein the wearable device comprises at least one other sensor, wherein the at least one other sensor is configured to obtain the other biometric data, and wherein the operations further comprise comparing the digital output with the other biometric data obtained by the at least one other sensor.

19. The system of claim 11, wherein the other biometric data comprises at least one of: respiration data, movement data, blood pressure data, heart rate data, blood oxygen saturation data, or galvanic skin response data.

20. The system of claim 11, further comprising a housing, wherein the analog hardward, the ADC, and the controller are housed within the housing.

* * * * *